United States Patent
Paul

(10) Patent No.: US 8,067,633 B2
(45) Date of Patent: Nov. 29, 2011

(54) METHOD FOR THE SYNTHESIS OF (METH)ACRYLIC ESTERS CATALYSED BY A POLYOL TITANATE

(75) Inventor: Jean-Michel Paul, Metz (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/517,086

(22) PCT Filed: Nov. 30, 2007

(86) PCT No.: PCT/FR2007/052429
§ 371 (c)(1),
(2), (4) Date: Jan. 4, 2010

(87) PCT Pub. No.: WO2008/068444
PCT Pub. Date: Jun. 12, 2008

(65) Prior Publication Data
US 2010/0145092 A1    Jun. 10, 2010

(30) Foreign Application Priority Data
Dec. 5, 2006  (FR) ...................... 06 55306

(51) Int. Cl.
*C07C 67/02* (2006.01)
(52) U.S. Cl. ..................................... 560/217
(58) Field of Classification Search ........................ None
See application file for complete search history.

(56) References Cited

U.S. PATENT DOCUMENTS
4,851,568 A * 7/1989 Hurtel et al. ................. 560/222
5,637,689 A   6/1997 Herbst et al.
6,437,173 B1  8/2002 Hurtel et al.
2005/0119500 A1 * 6/2005 Ackermann et al. .......... 560/217

FOREIGN PATENT DOCUMENTS
GB          960005      6/1964

OTHER PUBLICATIONS

Deleuze, H. et al., "Polymer-Supported Titanates as Catalyst for Transesterification Reactions", Polymer, vol. 39, No. 24, 1998.
Lewis, N. et al., "A Highly Efficient Preparation of Methacrylate Esters Using Novel Solid Phase Titamium-Based Transesterification Catalysts", Synlett, No. Spec.ISS, pp. 957-959, 1999.
Schnurrenberger, P. et al., "Herstellung vn Methylestern durch Umesterung funktionalisierter Substrate mit Titalsaureestern als Katalysatoren", Helvetica Chimica Acta, vol. 65, Fasc 4, pp. 1197-1201, 1982.
English translation of Schnurrenberger, P. et al., "Synthesis of Methyl Esters by Substrates with Titanic Acid Esters as Catalysts Functionalized by Transesterification," Helvetica Chimica Acta, vol. 65, Fasc. 4, No. 110, 1197-1201 (1982).

* cited by examiner

*Primary Examiner* — Sudhakar Katakam
(74) *Attorney, Agent, or Firm* — Kimberly R. Hild

(57) ABSTRACT

The subject of the invention is a method for the synthesis of (meth)acrylic esters by transesterification in the presence of a catalyst corresponding to the formula $[(R'O)_3Ti]_xR''$ in which R' is a linear or branched alkyl radical having from 2 to 8 carbon atoms which may contain heteroatoms or R' is a phenyl radical, R' is a polyfunctional radical, originating from a polyol $R'(OH)_x$ comprising x alcohol functional groups and x is an integer ranging from 2 to 6. The method according to the invention is particularly well suited to the synthesis of dialkylaminoalkyl (meth)acrylates from methyl (meth)acrylate and a dialkylaminoalcohol.

9 Claims, No Drawings

METHOD FOR THE SYNTHESIS OF (METH)ACRYLIC ESTERS CATALYSED BY A POLYOL TITANATE

FIELD OF THE INVENTION

The present invention relates to a method for the synthesis of (meth)acrylic esters by transesterification using a polyol titanate-based catalyst.

BACKGROUND OF THE INVENTION

A method commonly used for producing (meth)acrylic esters is transesterification. It is known practice, for example according to documents GB 960 005, EP 298 867, EP 619 309 or EP 960 877, to prepare the (meth)acrylic esters of formula (I):

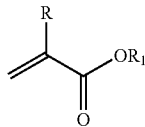

in which R is a hydrogen atom or a methyl group, and it being possible for $R_1$ to be a linear or branched alkyl radical, or a cyclic aliphatic, aryl, alkylaryl or arylalkyl radical, which may contain heteroatoms, according to a method of transesterification by reacting an alkyl (meth)acrylate of formula (II):

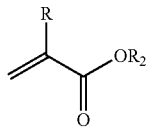

in which R has the abovementioned meaning and it being possible for $R_2$ to be a linear or branched alkyl group having from 1 to 4 carbon atoms,
with an alcohol of formula (III):

$R_1$—OH in which $R_1$ has the abovementioned meaning.

During the synthesis, light alcohol $R_2$—OH is generated and is eliminated in the form of an azeotrope with the light alkyl (meth)acrylate (II).

The synthesis of (meth)acrylic esters by transesterification is generally carried out in the presence of a catalyst. The choice of the catalyst depends on various criteria, in particular on the nature of the alkyl (meth)acrylate (II) used, but also on the nature of the alcohol (III) used to prepare the (meth) acrylic ester. In addition to the criteria of efficiency and selectivity, other factors may be involved, such as commercial availability, cost or toxicity of the catalyst.

As examples of catalysts described in the literature for catalyzing the preparation of (meth)acrylic esters by transesterification, mention may in particular be made of:

Acid catalysts, such as methanesulfonic acid or para-toluenesulfonic acid: these catalysts have the drawback of being relatively nonselective and corrosive.

Basic catalysts, such as alkali metal salts or alkaline-earth metal salts: these catalysts are active but prove to be relatively nonselective.

Chelates of titanium, zirconium, iron, zinc or calcium with 1,3-dicarbonyl compounds, such as Ti, Zr, Fr, Zn or Ca acetylacetonates: these compounds are active and selective, but generate acetylacetone and are sensitive to the presence of 1,2- or 1,3-diols. In addition, they rapidly lose their activity and as a result are not recyclable.

Tin derivatives, such as dialkyl tin oxides, dialkyl tin dialkoxides and dialkyl tin diesters, in particular di-n-butyltin oxide (DBTO and homologs thereof), are generally active and selective. However, with these catalysts, there is the problem of their elimination in the distillation residues owing to the toxicity of tin.

Titanium alkoxides, such as tetraalkyl (ethyl, n-propyl, isopropyl, n-butyl, etc.) titanates, or alternatively dimethylaminoethyl titanate or titanium phenolate: they are catalysts that are generally active and selective, but sensitive to water.

Enzymes of which the use is described in patent JP 04 079889.

Titanium alkoxides have been found to be active and selective catalysts and the use thereof is recommended in particular in methods for the synthesis of dialkylaminoalkyl (meth)acrylates.

Mention may be made of European patent EP 298 867, which describes in particular the preparation of N,N-dimethylaminoethyl acrylate (DMAEA) in the presence of tetraethyl titanate according to a method of transesterification by reacting ethyl acrylate with dimethylaminoethanol.

In patent EP 960 877, the dialkylaminoalkyl (meth)acrylates are obtained in the presence of a transesterification catalyst chosen from tetrabutyl, tetraethyl and tetra-(2-ethyl-hexyl) titanates, using methyl or ethyl (meth)acrylate with an amino alcohol. In order to obtain a product of high purity, it is, however, necessary to first carry out tailing, i.e. elimination of the catalyst and of the heavy products, followed by topping and a final rectification of the crude reaction mixture.

When it is a question of producing a dialkylaminoalkyl (meth)acrylate, such as DMAEA, by transesterification starting from methyl (meth)acrylate, it is difficult to envision using a titanium alkoxide such as tetraethyl titanate, because of the gradual appearance of a white precipitate which is completely insoluble in the reaction medium, which proves to be tetramethyl titanate. This is because, in the presence of the methanol generated during the transesterification, there is an exchange of ligands with the titanate used, and formation of methyl titanates, of which tetramethyl titanate, which is insoluble, is the ultimate end point. In addition to the phenomenon of deactivation of the catalyst and, consequently, slowing down of the reaction kinetics, clogging of the reactor and of the ancillary equipment thereof also occurs, which is unacceptable on the industrial scale.

In the article POLYMER, vol. 39, no. 24, (1998), pages 6109-6114, Deleuze H. et al., describe the transesterification of methyl acrylate with 2-ethyl-hexanol in the presence of a supported catalyst which is in the form of polymer beads onto which titanate functions are grafted, the advantage being that of being able to easily separate the catalyst from the reaction medium by filtration.

The article by N. Lewis et al., in SYNLETT, No. Spec. ISS, 1999, pages 957-959, describes the transesterification of methyl methacrylate with bromoundecanol in the presence of a catalyst constituted of a titanate grafted onto a polystyrene support, which can be readily separated from the reaction medium by simple filtration.

SUMMARY OF THE INVENTION

A family of catalysts based on titanium and polyol has now been found, which make it possible to catalyze the synthesis of (meth)acrylic esters by transesterification, in particular, starting from methyl (meth)acrylate, without any deactivation of the catalyst or clogging of the reactor being observed. These catalysts, in addition to the fact that they are very active and selective, have the advantage of not allowing any solid to precipitate during the reaction, unlike the abovementioned alkyl titanates which generate insoluble methyl titanate in the presence of methanol. The reaction of ligand exchange with the light alcohol generated during the reaction, such as, for example, methanol, or with the alcohol used for the reaction, does not result in species that are insoluble in the reaction medium. The problems related to the impurities generated by the transesterification of the catalyst are thus avoided, and the purification of the (meth)acrylic ester is simplified. Compared with the conventional tin-based catalysts, the polyol titanates have the advantage of not being toxic, thereby facilitating the destruction of the final distillation residues by incineration.

DETAILED DESCRIPTION OF THE INVENTION

The subject of the present invention is therefore a method for the synthesis of (meth)acrylic esters of formula (I):

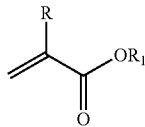

in which R is a hydrogen atom or a methyl group, and $R_1$ is a linear or branched alkyl radical, or a cyclic aliphatic, aryl, alkylaryl or arylalkyl radical, containing from 5 to 40 carbon atoms, or a linear or branched alkyl radical containing at least one heteroatom and from 3 to 40 carbon atoms, by reacting an alkyl (meth)acrylate of formula (II):

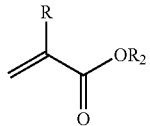

in which R has the abovementioned meaning and $R_2$ is a methyl group, with an alcohol of formula (III):

in which $R_1$ has the abovementioned meaning, in the presence of a transesterification catalyst and of at least one polymerization inhibitor, characterized in that the catalyst is a polyol titanate of formula (IV) $[(R'O)_3TiO]_xR''$ in which R' is a linear or branched alkyl radical having from 2 to 8 carbon atoms which may contain heteroatoms or R' is a phenyl radical, R'' is a linear or branched alkylene group having from 2 to 12 carbon atoms and which may comprise oxygen atoms and/or aliphatic or aromatic rings, originating from a polyol $R''(OH)_x$ comprising x alcohol functions and x is an integer ranging from 2 to 6.

The polyol titanates of formula (IV) can be prepared by reacting a titanium alkoxide $Ti(OR')_4$ with a polyol $R''(OH)_x$, x representing the number of alcohol functions of the polyol, according to the reaction (A):

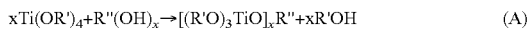

The reaction is preferably carried out in a solvent medium, the ligand exchange being carried out by eliminating the light alcohol R'OH generated by distillation, optionally in the form of an azeotrope with the solvent. The ligand exchange can generate other forms of polyol titanates, as by-products, during the reaction.

The formation of an ethylene glycol titanate, known as Gly-Ti, from tetraethyl titanate and ethylene glycol, according to the reaction:

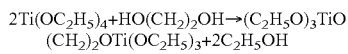

has been described by Seebach in the article Helvetica Chimica Acta, vol. 65, Fasc. 4 (1982) No. 110 pages 1197-1201.

By using the Gly-Ti as catalyst, Seebach was able to prepare nonacrylic methyl esters from nonacrylic esters and methanol, without generating insoluble tetramethyl titanate.

As solvents that can be used for the reaction (A), mention may be made, in a nonlimiting manner, of cyclohexane, toluene, heptane or hexane.

The reaction (A) is carried out at the boiling point of the alcohol R'OH or of the solvent/R'OH azeotrope at the operating pressure.

The reaction may be carried out at atmospheric pressure or under vacuum.

After complete elimination of the solvent, the compound formed can be used as catalyst.

In formula (IV), the R' radical is, by way of example, the ethyl, n-propyl, isopropyl, n-butyl, isobutyl, 2-ethylhexyl, dimethylaminoethyl or phenyl radical, or mixtures thereof.

As starting titanates $Ti(OR')_4$ use may be made, by way of examples, of tetraalkyl titanates such as tetraethyl titanate, tetrapropyl titanate, tetraisopropyl titanate, tetrabutyl titanate, tetraisobutyl titanate or tetra-2-ethylhexyl titanate, or else dimethylaminoethyl titanate or titanium phenolate, and also mixtures thereof.

The polyols $R''(OH)_x$ that can be used to prepare the polyol titanates are polyols of functionality x ranging from 2 to 6; diols or trials will preferably be chosen.

By way of examples of polyols, mention may be made of: ethylene glycol, propylene glycol, 1,3-butanediol, 1,4-butanediol, 1,6-hexanediol, neopentyl glycol, diethylene glycol, triethylene glycol, tetraethylene glycol, glycerol, dipropylene glycol, tripropylene glycol, cyclohexanedimethanol, bisphenol-A, trimethylolpropane, pentaerythritol, ditrimethylol-propane and dipentaerythritol.

Preferably, the dials for which the R'' radical is a linear alkylene group having from 2 to 6 carbon atoms which may comprise oxygen atoms, such as ethylene glycol, diethylene glycol, 1,3-butanediol, 1,4-butanediol or 1,6-hexanediol, will be used.

The molar ratio of the titanate $Ti(OR')_4$ to the polyol $R''(OH)_x$ according to the reaction (A) is equal to the number of alcohol functions of the polyol. Preferably, a slightly higher molar ratio will be used for a diol, preferably a molar ratio of between 2.2 and 2 for a dial, and a slightly lower molar ratio will be used for polyols comprising more than two alcohol functions, i.e., for example, a molar ratio of between 2.8 and 3 for a triol, or between 3.8 and 4 for a polyol comprising four alcohol functions.

The polyol titanates of formula (IV) may be in liquid or solid form. Liquid polyol titanates are preferred.

The polyol titanates of formula (IV) are particularly suitable for the synthesis of the compounds of formula (I) in which $R_1$ is a dialkylaminoalkyl radical originating from an amino alcohol of formula $(R_3)(R_4)$ N-A-OH in which $R_3$ and $R_4$, which may be identical or different, are an alkyl radical containing 1 to 5 carbon atoms, and A is a linear or branched alkylene radical containing from 1 to 5 carbon atoms.

The method according to the invention is used in particular for preparing dimethylaminoethyl acrylate (DMAEA), dimethylaminopropyl acrylate, diethyl-aminoethyl acrylate, tert-butylaminoethyl acrylate or dimethylaminoethyl methacrylate (DMAEMA).

Preferably, the light alkyl (meth)acrylate (II) is methyl acrylate.

Methanol is generated during the synthesis, and is eliminated in the form of an azeotrope with the methyl (meth) acrylate (II).

In the method according to the invention, the catalyst is used in a proportion of 0.001 to 0.02 mol, preferably from 0.005 to 0.01 mol per mole of alcohol (III).

A methyl (meth)acrylate (II) to alcohol (III) molar ratio of between 2 and 5, preferably between 2 and 4, is preferably chosen.

The reaction temperature is generally between 80 and 110° C. and the pressure is generally maintained between 0.025 bar and atmospheric pressure. Preferably, the reaction temperature is between 90 and 110° C. and the pressure is of the order of 0.5 bar to atmospheric pressure.

As polymerization inhibitor, use is made of phenothiazine, hydroquinone, hydroquinone monomethyl ether, di-tert-butyl-para-cresol (BHT), para-phenylenediamine, TEMPO (2,2,6,6-tetramethyl-1-piperidinyloxy), di-tert-butylcatechol, or TEMPO derivatives, alone or as a mixture, in a proportion of from 100 to 5000 ppm relative to the initial charge, preferably between 500 and 3000 ppm.

The method according to the invention is particularly advantageous since there is no formation of insoluble tetramethyl titanate in the reaction mixture. The yields of the method according to the invention with respect to the alcohol (III) are high and most commonly greater than 95%. The final distillation residues containing the catalyst, which do not have the toxic nature of tin-based catalysts, can be incinerated without difficulty.

The following examples illustrate the present invention without, however, limiting the scope thereof. The percentages are expressed as percentages by weight.

EXAMPLE 1

Preparation of a TIPOL1 Catalyst

The following are charged to a stirred reactor heated by circulation of a thermostatically controlled oil in a jacket and surmounted by a multiknit-packed distillation column with top glycol-water condenser, reflux ratio head, vacuum distillation receiver, and collecting vessels and traps:
  200 g of a mixture constituted of 80% of tetraethyl titanate and 20% of tetraisopropyl titanate (sold under the name Vertec AC 560 by Johnson Matthey)
  24.8 g of ethylene glycol
  300 g of cyclohexane.

The reaction mixture is refluxed at atmospheric pressure for 3 h. The light alcohols, ethanol and isopropanol, released during the ligand exchange, are eliminated by distillation in the form of azeotropes with the cyclohexane.

The residual cyclohexane is then distilled. In the end, 195 g of crude product, which is in the form of a slightly viscous orange liquid (TIPOL1), are obtained.

EXAMPLE 2

Synthesis of dimethylaminoethyl acrylate (DMAEA)

The following are charged to the reactor described in example 1:
  595 g of methyl acrylate (MA)
  173.5 g of N,N-dimethylaminoethanol
  1.5 g (2000 ppm relative to the charge) of phenothiazine
  0.75 g (1000 ppm relative to the charge) of BHT (di-tert-butyl-para-cresol).

Throughout the entire synthesis, air is bubbled into the reaction mixture.

The water present in the charge, originating from the alcohol, is eliminated by distillation at atmospheric pressure, in the form of an MA/water azeotrope.

After the above drying phase, a further amount of methyl acrylate, corresponding to the mass of the drying fraction, is introduced. 6.85 g (0.008 mol) of TIPOL1 are subsequently introduced.

The reaction is carried out at atmospheric pressure with a temperature in the reaction medium of between 85 and 95° C. The methanol formed during the reaction is eliminated as it forms, in the form of an MA/methanol azeotrope, at a column-top temperature of between 61.9 and 63.5° C. The conversion rate is monitored by chromatographic analysis of the azeotrope. The conversion rate reaches 97.8% after 270 min of reaction.

The crude product obtained at this stage of the synthesis is completely clear. The presence of solid is not detected therein. The yield and the selectivity of the operation are, respectively, 96.6% and 98.7%.

EXAMPLE 3 (COMPARATIVE)

Example 2 is repeated using, everything else being otherwise equal, tetraethyl titanate as catalyst (4.1 g).

After reaction for 10 h, the rate of conversion of the N,N-dimethylaminoethanol is 70% and a solid deposit is observed in the reactor, which is found to be insoluble methyl titanate.

EXAMPLE 4 (COMPARATIVE)

Example 2 is repeated using, everything else being otherwise equal, tetraisopropyl titanate as catalyst (4.5 g).

After reaction for 5 h at a temperature of between 84 and 88° C., the rate of conversion of the N,N-dimethylaminoethanol is 92%. As in example 3, a deposit is observed in the crude reaction product, which is found to be insoluble methyl titanate.

EXAMPLE 5

Two polyol titanates, called TIPOL2 and TIPOL3, are prepared under the conditions of example 1 using isopropyl titanate and, respectively, ethylene glycol and propylene glycol with an isopropyl titanate/diol molar ratio=2/1.

These two polyol titanates are subsequently used as catalysts for the synthesis of DMAEA according to the protocol used in example 2.

The crude reaction products obtained with these catalysts are completely liquid and clear.

The conversion rate and selectivity are identical with TIPOL2 or TIPOL3, and are 98% and 96%, respectively.

The invention claimed is:

1. A method for the synthesis of (meth)acrylic esters of formula (I):

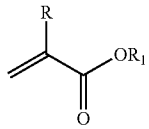

in which R is a hydrogen atom or a methyl group, and $R_1$ is a linear or branched alkyl radical, or a cyclic aliphatic, aryl, alkylaryl or arylalkyl radical, containing from 5 to 40 carbon atoms, or a linear or branched alkyl radical containing at least one heteroatom and having from 3 to 40 carbon atoms, comprising:

reacting an alkyl (meth)acrylate of formula (II):

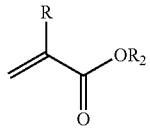

in which R has the abovementioned meaning and $R_2$ is a methyl group, with an alcohol of formula (III):

in which $R_1$ has the abovementioned meaning, in the presence of a transesterification catalyst and of at least one polymerization inhibitor, characterized in that the catalyst is a polyol, titanate of formula (IV) $[(R'O)_3TiO]_xR''$ in which R' is selected from a linear or branched alkyl radical having from 2 to 8 carbon atoms which may contain heteroatoms or a phenyl radical, R'' is a linear or branched alkylene group having from 2 to 12 carbon atoms and which may comprise oxygen atoms and/or aliphatic or aromatic rings, originating from a polyol $R''(OH)_x$ comprising x alcohol functions and x is an integer ranging from 2 to 6, under conditions effective to achieve a yield greater than 95%.

2. The method as claimed in claim 1, characterized in that the catalyst of formula (IV) is prepared by reacting a titanium alkoxide $Ti(OR')_4$ with a polyol $R''(OH)_x$, x representing the number of alcohol functions of the polyol, according to the reaction (A):

preferably in a solvent medium.

3. The method as claimed in claim 1, characterized in that the R'' radical is a linear alkylene group having from 2 to 6 carbon atoms which may comprise oxygen atoms.

4. The method as claimed in claim 1, characterized in that the R'' radical originates from a diol or a triol.

5. The method as claimed in claim 1, characterized in that the R'' radical originates from ethylene glycol, diethylene glycol, 1,3-butanediol, 1,4-butanediol or 1,6-hexanediol.

6. The method as claimed in claim 1, characterized in that the R' radical is selected from ethyl, n-propyl, isopropyl, n-butyl, isobutyl, 2-ethylhexyl, dimethylaminoethyl, phenyl, or mixtures thereof.

7. The method as claimed in claim 1, characterized in that the catalyst is used in a proportion of from 0.001 to 0.02 mol per mole of alcohol (III).

8. The method as claimed in claim 1, characterized in that the $R_1$ radical is a dialkylaminoalkyl radical originating from an amino alcohol of formula $(R_3)(R_4)N$-A-OH in which $R_3$ and $R_4$, which may be identical or different, are an alkyl radical containing 1 to 5 carbon atoms, and A is a linear or branched alkylene radical containing from 1 to 5 carbon atoms.

9. The method as claimed in claim 1, wherein said (meth)acrylic eter is selected from dimethylaminoethyl acrylate (DMAEA), dimethylaminopropyl acrylate, diethylaminoethyl acrylate, tert-butylaminoethyl acrylate or dimethylaminoethyl methacrylate (DMAEMA).

* * * * *